(12) United States Patent
Hsueh et al.

(10) Patent No.: US 9,839,906 B1
(45) Date of Patent: Dec. 12, 2017

(54) CATALYST AND METHOD FOR SYNTHESIZING CYCLIC CARBONATE BY THE SAME

(71) Applicant: Industrial Technology Research Institute, Hsinchu (TW)

(72) Inventors: Mao-Lin Hsueh, Pingtung County (TW); Yi-Zhen Chen, Tainan (TW); Kuo-Chen Shih, Kaohsiung (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 15/465,611

(22) Filed: Mar. 22, 2017

(30) Foreign Application Priority Data

Dec. 7, 2016 (TW) .............................. 105140428 A

(51) Int. Cl.
*B01J 31/22* (2006.01)
*C07D 317/34* (2006.01)

(52) U.S. Cl.
CPC ........ *B01J 31/2213* (2013.01); *C07D 317/34* (2013.01); *B01J 2531/42* (2013.01)

(58) Field of Classification Search
CPC .................................................. B01J 31/2213
USPC ......................................................... 549/229
See application file for complete search history.

(56) References Cited

U.S. PATENT DOCUMENTS

| | | | |
|---|---|---|---|
| 4,663,467 | A | 5/1987 | Kruper, Jr. et al. |
| 6,933,394 | B2 | 8/2005 | Sakakura et al. |
| 7,365,214 | B2 | 4/2008 | Srinivas et al. |
| 7,728,164 | B2 | 6/2010 | Lange |
| 8,653,290 | B2 | 2/2014 | Kaita et al. |
| 8,956,989 | B2 | 2/2015 | Allen et al. |
| 9,211,534 | B2 | 12/2015 | Ema et al. |
| 9,242,955 | B2 | 1/2016 | North |
| 2015/0119584 | A1 | 4/2015 | Yeh et al. |

FOREIGN PATENT DOCUMENTS

| | | |
|---|---|---|
| CN | 1189246 | 2/2005 |
| CN | 101084179 | 12/2007 |
| CN | 101177481 | 5/2008 |
| CN | 102574971 | 7/2012 |
| CN | 102671703 | 9/2012 |
| CN | 102702022 | 10/2012 |
| CN | 102775378 | 11/2012 |
| CN | 103319451 | 9/2013 |
| CN | 103447091 | 12/2013 |
| CN | 103752344 | 4/2014 |
| CN | 103906787 | 7/2014 |
| CN | 104496959 | 4/2015 |
| CN | 104725344 | 6/2015 |
| CN | 103987714 | 3/2016 |
| JP | 2006151891 | 6/2006 |
| TW | I423993 | 1/2014 |

OTHER PUBLICATIONS

Yi-Chang Liu, et al., "A Highly Efficient Catalyst for the "Living" and "Immortal" Polymerization of ε-Caprolactone and l-Lactide" Macromolecules, vol. 34, No. 18, Jul. 31, 2001, pp. 6196-6201.
Michael North, et al., "Mechanism of Cyclic Carbonate Synthesis from Epoxides and CO2," Angew. Chem., vol. 121, No. 16, Apr. 6, 2009, pp. 2990-2992.
Xiao-Bing Lu, et al., "Cobalt catalysts for the coupling of CO2 and epoxides to provide polycarbonates and cyclic carbonates," Chem. Soc. Rev., vol. 41, No. 4, Feb. 21, 2012, pp. 1462-1484.
William Clegg, et al., "Cyclic Carbonate Synthesis Catalysed by Bimetallic Aluminium—Salen Complexes," Chem. Eur. J., vol. 16, No. 23, Jun. 18, 2010, pp. 6828-6843.
Tadashi Ema, et al., "A bifunctional catalyst for carbon dioxide fixation: cooperative double activation of epoxides for the synthesis of cyclic carbonates," Chem. Commun., vol. 48, No. 37, May 11, 2012, pp. 4489-4491.
Ahlam Sibaouih, et al., "Facile synthesis of cyclic carbonates from CO2 and epoxides with cobalt(II)/onium salt based catalysts," Applied Catalysis A: General, vol. 365, No. 2, Aug. 31, 2009, pp. 194-198.
Vincenzo Caló, et al., "Cyclic Carbonate Formation from Carbon Dioxide and Oxiranes in Tetrabutylammonium Halides as Solvents and Catalysts," Organic Letters, vol. 4, No. 15, Jul. 1, 2002, pp. 2561-2563.
Jing Guan, et al., "Progress in Study of Non-Isocyanate Polyurethane," Ind. Eng. Chem. Res., vol. 50, Jun. 1, 2011, pp. 6517-6527.
Xiying Fu, et al., "Pd/C as a high efficient and reusable catalyst for cycloaddition of CO2 to epoxides," Journal of CO2 Utilization, vol. 14, Jun. 2016, pp. 31-36.
Alexander Barthel, et al., "Highly integrated CO2 capture and conversion: direct synthesis of cyclic carbonates from industrial flue gas," Green Chem., vol. 18, Feb. 8, 2016, pp. 3116-3123.

(Continued)

*Primary Examiner* — Taofiq A Solola
(74) *Attorney, Agent, or Firm* — JCIPRNET

(57) ABSTRACT

A catalyst and a method for synthesizing cyclic carbonate using the catalyst are provided. The catalyst includes a metal complex shown in formula (I):

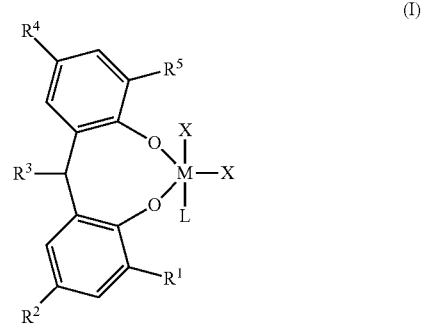

wherein $R^1$, $R^2$, $R^4$, and $R^5$ are independently a C1-C25 alkyl group, a C1-C25 alkoxy group, a C3-C8 cycloalkyl group, a C6-C25 aryl group, a C6-C25 aryloxy group, a C7-C25 aralkyl group, a C7-C25 aralkoxy group, or halogen; $R^3$ is hydrogen, a C1-C25 alkyl group, a C3-C8 cycloalkyl group, a C6-C25 aryl group, a C6-C25 aryloxy group, a C7-C25 aralkyl group, or a C7-C25 aralkoxy group; M is Sn or Ti; X is Cl, Br, I, or OAc; and L represents ether or furan.

12 Claims, 1 Drawing Sheet

(56) References Cited

OTHER PUBLICATIONS

Sanny Verma, et al., "Titanium-based zeolitic imidazolate framework for chemical fixation of carbon dioxide," Green Chem., vol. 18, Aug. 3, 2016, pp. 4855-4858.
Mirza Cokoja, et al., "Synthesis of Cyclic Carbonates from Epoxides and Carbon Dioxide by Using Organocatalysts," ChemSusChem, vol. 8, No. 15, Aug. 10, 2015, pp. 2436-2454.
Xingfeng Sheng, et al., "Highly efficient and quantitative synthesis of a cyclic carbonate by iron complex catalysts," Polyhedron, vol. 74, May 28, 2014, pp. 129-133.
Laia Cuesta-Aluja, et al., "Highly active and selective Zn(II)—NN'O Schiff base catalysts for the cycloaddition of CO2 to epoxides," Journal of CO2 Utilization, vol. 14, Jun. 2016, pp. 10-22.
"Notice of allowance of Taiwan Counterpart Application", dated Aug. 17, 2017, p. 1-p. 5.

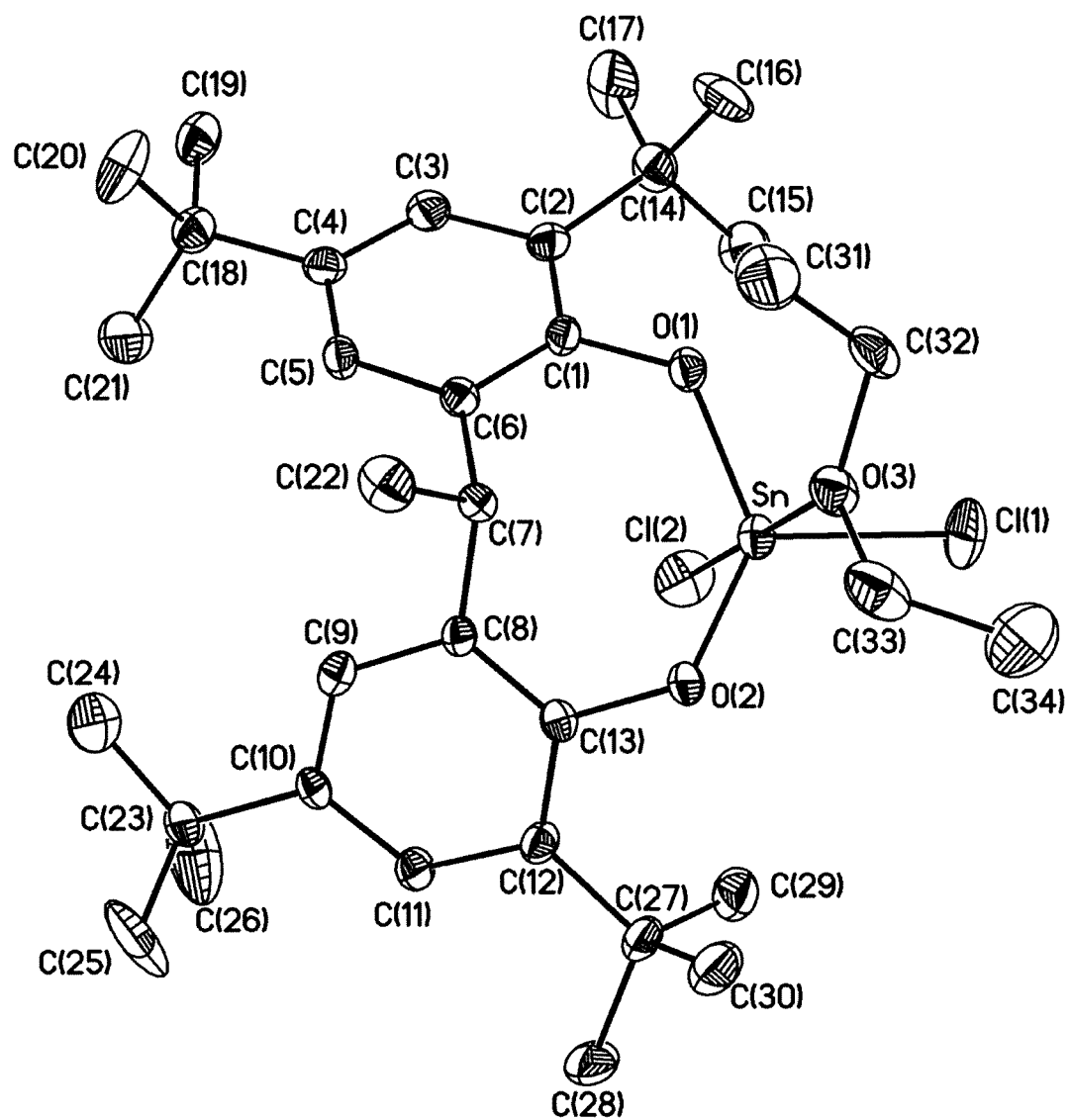

CATALYST AND METHOD FOR SYNTHESIZING CYCLIC CARBONATE BY THE SAME

CROSS-REFERENCE TO RELATED APPLICATION

This application claims the priority benefit of Taiwan application serial no. 105140428, filed on Dec. 7, 2016. The entirety of the above-mentioned patent application is hereby incorporated by reference herein and made a part of this specification.

TECHNICAL FIELD

The disclosure relates to a catalyst and a method for synthesizing cyclic carbonate by the same.

BACKGROUND

Polyurethane (PU) is mainly applied in areas such as transportation, construction, textiles, electromechanics, aviation, medical treatment, coating, and synthetic leather, and is used in a wide variety of products with extensive applications, and has a rising demand. However, since PU is obtained from highly-toxic isocyanate and polyol, and the raw material of isocyanate is phosgene with even greater toxicity, significant harm is readily incurred to the human body during the raw material production process and coating processing. Moreover, isocyanate is sensitive to the humidity in the environment and reacts with water to form carbon dioxide gas, such that bubbles formation in the coating layer are occurred and sealing properties are reduced, and the usability of isocyanate are affected as a result.

Therefore, research efforts toward the development of a non-isocyanate polyurethane material are currently done. In many studies, non-isocyanate polyurethane (NIPU) materials prepared by cyclic carbonate and an amine compound have received the most attention.

NIPU is mainly obtained by reacting cyclic carbonate with an amine compound, and since the synthesis method thereof can avoid the use of an isocyanate compound having greater toxicity, the resulting product is a green material garnering increasing attention.

The key raw material of the non-isocyanate material is a cyclic carbonate compound, and the compound can be obtained by reacting carbon dioxide with an epoxy compound under the catalysis of a catalyst. Currently, the catalyst used in the synthesis of a cyclic carbonate compound has strict reaction conditions and low reaction conversion rate, and the thresholds of the cyclic carbonate process and the commercial mass production of the NIPU material are increased, and therefore how to effectively increase the reaction efficiency of an epoxy compound and carbon dioxide and develop a catalysis system having higher reactivity that can produce polycyclic carbonate under mild conditions have become an important research topic in recent years.

SUMMARY

The catalyst of the disclosure includes the metal complex shown in formula (I).

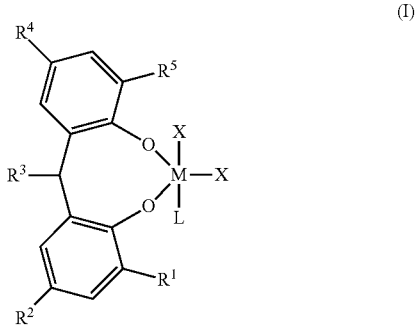

(I)

wherein $R^1$, $R^2$, $R^4$, and $R^5$ are independently a C1-C25 alkyl group, a C1-C25 alkoxy group, a C3-C8 cycloalkyl group, a C6-C25 aryl group, a C6-C25 aryloxy group, a C7-C25 aralkyl group, a C7-C25 aralkoxy group, or halogen; $R^3$ is hydrogen, a C1-C25 alkyl group, a C3-C8 cycloalkyl group, a C6-C25 aryl group, a C6-C25 aryloxy group, a C7-C25 aralkyl group, or a C7-C25 aralkoxy group; M is Sn or Ti; X is Cl, Br, I, or OAc; and L represents ether or furan.

The synthesis method of a cyclic carbonate of the disclosure includes reacting an epoxy compound with carbon dioxide to form a cyclic carbonate compound in the presence of the aforementioned catalyst.

Several exemplary embodiments accompanied with figures are described in detail below to further describe the disclosure in details.

BRIEF DESCRIPTION OF THE DRAWINGS

The accompanying drawing is included to provide further understanding, and is incorporated in and constitutes a part of this specification. The drawing illustrates exemplary embodiment and, together with the description, serves to explain the principles of the disclosure.

FIG. 1 is a three-dimensional schematic diagram of the molecular structure of catalyst C-2 in synthesis example 2 of the disclosure.

DETAILED DESCRIPTION OF DISCLOSED EMBODIMENTS

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In an embodiment of the disclosure, the catalyst includes a metal complex as shown in formula (I).

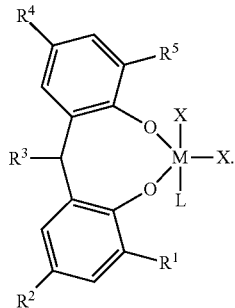

In formula (I), M is tin (Sn) or titanium (Ti).
In formula (I), X is Cl, Br, I, or OAc.
In formula (I), L is ether or furan.

Specific examples of the ether or furan can include, but are not limited to, methyl ether, ethyl ether, methyl ethyl ether, dipropyl ether, methyl propyl ether, ethyl propyl ether, dibutyl ether, isodibutyl ether, isopropyl ether, furan, tetrahydrofuran, dihydropyran, tetrahydropyran.

In formula (I), $R^1$, $R^2$, $R^4$, and $R^5$ are independently a C1-C25 alkyl group, a C1-C25 alkoxy group, a C3-C8 cycloalkyl group, a C6-C25 aryl group, a C6-C25 aryloxy group, a C7-C25 aralkyl group, a C7-C25 aralkoxy group, or halogen; $R^3$ is hydrogen, a C1-C25 alkyl group, a C3-C8 cycloalkyl group, a C6-C25 aryl group, a C6-C25 aryloxy group, a C7-C25 aralkyl group, or a C7-C25 aralkoxy group.

The C1-C25 alkyl group can be unsubstituted or optionally substituted by one or a plurality of a substituent, and specific examples can include, but are not limited to, methyl group, ethyl group, n-propyl group, 1-methylethyl, n-butyl group, 1-methylpropyl, 2-methylpropyl, 1,1'-dimethylethyl, n-pentyl group, 1-methylbutyl, 2-methylbutyl, 3-methylbutyl, 2,2'-dimethylpropyl, 1-ethylpropyl, n-hexyl group, 1,1'-dimethylpropyl, 1,2-dimethylpropyl, 1-methylpentyl, 2-methylpentyl, 3-methylpentyl, 4-methylpentyl, 1,1'-dimethylbutyl, 1,2-dimethylbutyl, 1,3-dimethylbutyl, 2,2'-dimethylbutyl, 2,3-dimethylbutyl, 3,3'-dimethylbutyl, 1-ethylbutyl, 2-ethylbutyl, 1,1',2-trimethylpropyl, 1,2,2'-trimethylpropyl, 1-ethyl-1-methylpropyl, 1-ethyl-2-methylpropyl, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, or n-eicosyl group.

The C1-C25 alkoxy group can be unsubstituted or optionally substituted by one or a plurality of a substituent, and specific examples can include, but are not limited to, methoxy group, ethoxy group, isopropoxy group, n-propoxy group, 1-methylpropoxy, n-butoxy group, n-pentoxy group, 2-methylpropoxy, 3-methylbutoxy, 1,1'-dimethylpropoxy, 2,2'-dimethylpropoxy, hexyloxy group, 1-methyl-1-ethylpropoxy, heptyloxy group, octyloxy group, or 2-ethylhexyloxy.

The C3-C8 cycloalkyl group can be unsubstituted or optionally substituted by one or a plurality of a substituent, and specific examples can include, but are not limited to, cyclopropyl group, cyclobutyl group, cyclopentyl group, cyclohexyl group, cycloheptyl group, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, or cyclooctyl group.

The C6-C25 aryl group can be unsubstituted or optionally substituted by one or a plurality of a substituent, and specific examples can include, but are not limited to, phenyl group, naphthyl group, 2-methylphenyl, 3-methylphenyl, 4-methylphenyl, 2-ethylphenyl, 1,1'-dimethylphenyl, 2-tert-butylphenyl, 3-tert-butylphenyl, 4-tert-butylphenyl, 3-ethylphenyl, 4-ethylphenyl, 2,4-di-tert-butylphenyl, 3-methyl-6-tert-butylphenyl, 2,4-di-tert-butylphenyl, 2-methoxyphenyl, 3-methoxyphenyl, 4-methoxyphenyl, 2,4-dimethoxyphenyl, 2-ethoxyphenyl, 3-ethoxyphenyl, 4-ethoxyphenyl, 2,4-diethoxyphenyl, 3-methoxy-6-tert-butylphenyl, or p-adamantylphenyl.

The C6-C25 aryloxy group can be unsubstituted or optionally substituted by one or a plurality of a substituent, and specific examples can include, but are not limited to, phenoxy group, 2-methylphenoxy, 3-methylphenoxy, 4-methylphenoxy, 4-methoxyphenoxy, or 4-tert-butylphenoxy.

The C7-C25 aralkyl group can be unsubstituted or optionally substituted by one or a plurality of a substituent, and specific examples can include, but are not limited to, benzyl group, α-methylbenzyl, α,α-dimethylbenzyl, 2-methylbenzyl, 3-methylbenzyl, 4-methylbenzyl, 2,4-dimethylbenzyl, 2,6-dimethylbenzyl, or 4-tert-butylbenzyl.

The C7-C25 aralkyloxy group can be unsubstituted or optionally substituted by one or a plurality of a substituent, and specific examples can include, but are not limited to, benzyloxy group, 4-methylbenzyloxy, 4-methoxybenzyloxy, or 3-phenoxybenzyloxy.

The halogen is, for instance, fluorine, chlorine, bromine, or iodine.

In an embodiment, M in formula (I) is tin, and X is Cl or Br. L is ether or tetrahydrofuran. $R^1$, $R^2$, $R^4$, and $R^5$ in formula (I) are independently a C1-C4 alkyl group, a C1-C4 alkoxy group, a C5-C6 cycloalkyl group, a C6-C10 aryl group, a C6-C7 aryloxy group, or a C7-C9 aralkyl group; $R^3$ is hydrogen, a C1-C4 alkyl group, a C5-C6 cycloalkyl, a C6-C10 aryl group, a C6-C7 aryloxy group, or a C7-C9 aralkyl group. In particular, a C1-C4 alkyl group is methyl group, ethyl group, 1-methylethyl, n-propyl group, 1-methylpropyl, 2-methylpropyl, 1,1'-dimethylethyl, or n-butyl group; a C1-C4 alkoxy group is methoxy group, ethoxy group, n-propoxy group, isopropoxy group, 1-methylpropoxy, or n-butoxy group; a C5-C6 cycloalkyl group is a cyclopentyl group or a cyclohexyl group; a C6-C10 aryl group is phenyl group, 2-methylphenyl, 3-methylphenyl, 4-methylphenyl, 2-tert-butylphenyl, 3-tert-butylphenyl, 4-tert-butylphenyl, 2-methoxyphenyl, 3-methoxyphenyl, 4-methoxyphenyl, 2-ethoxyphenyl, 3-ethoxyphenyl, or 4-ethoxyphenyl; a C6-C7 aryloxy group is phenoxy group, 2-methylphenoxy, 3-methylphenoxy, 4-methylphenoxy, or 4-methoxyphenoxy; a C7-C9 aralkyl group is benzyl group, α-methylbenzyl, or α,α-dimethylbenzyl.

The metal complex represented by formula (I) can be prepared by reacting a bisphenol compound with a ligand containing an oxygen atom with a tin (IV) compound or a titanium compound in the presence of an amine compound, and the reaction formula (1) thereof is as shown below:

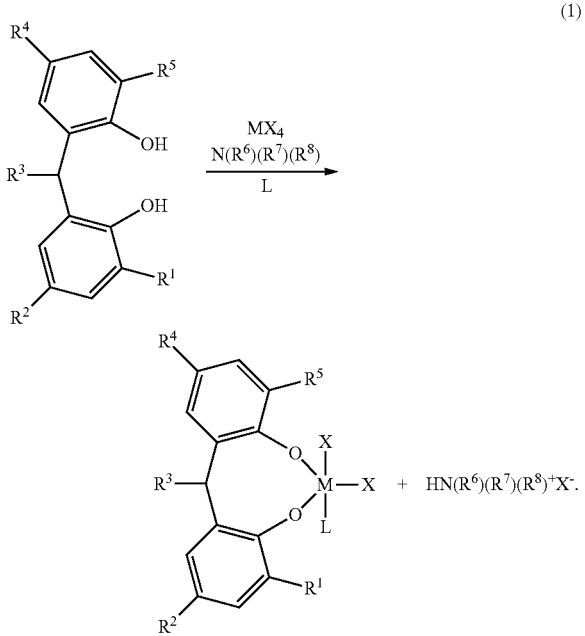

(1)

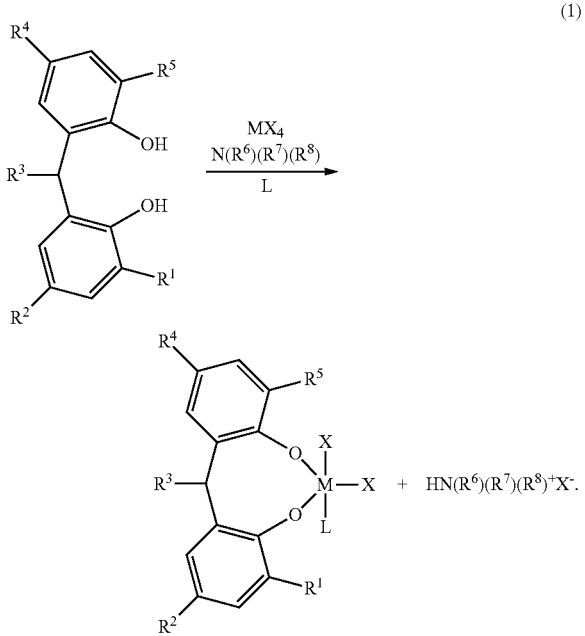

In formula (1), $R^1$, $R^2$, $R^3$, $R^4$, $R^5$, M, X, and L are as defined in formula (I) above. $R^6$, $R^7$, and $R^8$ are independently a C1-C25 alkyl group or a C6-C25 aryl group.

Therefore, in an embodiment of the disclosure, the catalyst can further include a quaternary ammonium salt as shown in formula (II).

(II)

In formula (II), $R^6$, $R^7$, and $R^8$ are as defined in formula (1); and X is as defined in formula (I).

Moreover, since the synthesis of the catalyst of the disclosure is as shown in formula (1), the molar ratio of the quaternary ammonium salt to the metal complex is between 0.01 and 2, such as between 1 and 2, but the disclosure is not limited thereto. In another embodiment, other quaternary ammonium salts can be added to further increase the conversion rate of the cyclic carbonate compound, wherein the molar ratio of the quaternary ammonium salt to the metal complex is between 0.01 and 5, such as between 0.5 and 3 or between 1 and 2, and if too much of the quaternary ammonium salt is added, then follow-up products may not be readily separated.

In the manufacturing method of an embodiment, an epoxy compound are reacted with carbon dioxide ($CO_2$) in the presence of the catalyst to form a cyclic carbonate compound. In particular, the epoxy compound can be represented by formula (III):

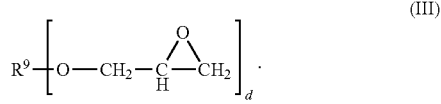

(III)

In formula (III), d is an integer of 1 to 6; $R^9$ is a functional group that can be substituted of an aliphatic compound, an alicyclic compound, an aromatic compound, an alkyl-substituted aromatic compound, polyether oligomer or polyester oligomer, or a combination thereof.

Specific examples of the epoxy compound can include, but are not limited to, poly(propylene glycol)diglycidyl ether (PPGDG), resorcinol diglycidyl ether (RDCE), diglycidyl ether of bisphenol-A (DGEBA), or 1,4-butanediol diglycidyl ether (BDGE).

Moreover, based on the amount of the epoxy compound, the concentration of the catalyst can be between $1 \times 10^{-6}$ mol % and 1 mol %, such as between $1 \times 10^{-2}$ mol % and 0.5 mol % or between $4 \times 10^{-3}$ mol % and $16 \times 10^{-3}$ mol %. When the concentration is more than 1 mol %, the yellowing issue of product readily occurs, and subsequent application properties are readily affected by excessive catalyst residue in the product. When the concentration is less than $1 \times 10^{-6}$ mol %, then the reaction efficiency is poor and the required reaction time is too long. In the present embodiment, the pressure ($CO_2$) is, for instance, between 0.1 atm and 100 atm or between 0.5 atm and 20 atm, and if the pressure is too high, then equipment specification requirements are strict and the production method of the cyclic carbonate compound lacks economic benefits. The reaction temperature is, for instance, between 50° C. and 200° C. or between 100° C. and 140° C. When the temperature is higher than 200° C., the system temperature readily becomes unmanageable with sudden increases; and when the temperature is lower than 50° C., the reaction efficiency is poor and the conversion rate is poor. The reaction time can be between 2 hours and 30 hours or between 2 hours and 24 hours, and a long reaction time is not beneficial to the conversion rate of the cyclic carbonate compound.

Since the catalyst in the above embodiment is a penta-coordinated catalyst, penta-coordinated tin is exemplified, wherein the sum of the bond angle of O(1)-Sn—O(2), the bond angle of O(1)-Sn—Cl, and the bond angle of O(2)-Sn—Cl is close to 360 degrees, indicating the plane formed by the 3 bonds connected to tin is almost planar. During the catalysis reaction, ether or furan ligand is removed and a very large three-dimensional space is provided to the Sn metal center, which is beneficial for the approach and ligand activation of an epoxy monomer, and therefore catalysis reaction is accelerated. In comparison, the tetrahedral structure of a tetra-coordinated catalyst cannot provide sufficient three-dimensional space for the approach and ligand activation of an epoxy monomer, and therefore the penta-coordinated catalyst can produce a cyclic carbonate compound having high conversion rate under mild reaction conditions.

A plurality of experiments is provided below to verify the effect of the disclosure, but the scope of the disclosure is not limited thereto.

Synthesis of Catalyst C-1

EDBP (2,2'-ethylidene-bis(4,6-di-tert-butylphenol), 50 mmol, 21.9 g) was placed in a 250 mL flask and nitrogen substitution was performed. Ether ($Et_2O$, 50 ml) was added and the mixture was sufficiently stirred and dissolved, and then $SnCl_4$ (tin (IV) tetrachloride, 50 mmol, 5.85 mL) was added. Tributylamine (also referred to as $NBu_3$, 100 mmol, 23.8 ml) was added to the mixture in an ice bath, and after stirring for 10 minutes, the ice bath was removed and the mixture was continuously reacted at room temperature for 1 hour. After the reaction, $Et_2O$ was drained to obtain a catalyst C-1: (EDBP)$SnCl_2$($Et_2O$)/$HNBu_3Cl$, and yield>99%.

Synthesis of Catalyst C-2

After $Et_2O$ was added to the catalyst C-1 and dissolved, hexane was slowly added and the mixture was stirred (hexane/Et$_2$O=100 mL/10 mL) to precipitate a large quantity of a yellow solid to obtain a catalyst C-2: (EDBP)SnCl$_2$ (Et$_2$O), and yield: 81%.

$^1$H NMR (CDCl$_3$, ppm) of the catalyst C-2: δ 7.34, 7.18 (dd, 4H, Ph, J=2.4 Hz); 4.44 (q, 1H, CH, J=6.4 Hz); 3.47 (q, 4H, OCH$_2$CH$_3$, J=6.8 Hz); 1.69 (d, 3H, J=6.8 Hz); 1.41 (s, 18H, C(CH$_3$)$_3$); 1.33-1.27 (m, 24H, C(CH$_3$)$_3$+OCH$_2$CH$_3$).

FIG. 1 is a three-dimensional schematic diagram of the molecular structure of the catalyst C-2 obtained by X-ray crystal diffraction analysis. In FIG. 1, the analysis produced a bond angle of 121.8 degrees for O(1)-Sn—O(2), a bond angle of 112.05 degrees for O(1)-Sn—Cl(1), and a bond angle of 119.59 degrees for O(2)-Sn—Cl(1), and therefore the catalyst C-2 is a penta-coordinated tin catalyst.

Synthesis of Catalyst C-3

EDBP (2,2'-ethylidene-bis(4,6-di-tert-butylphenol), 50 mmol, 21.9 g) was placed in a 250 mL flask and nitrogen substitution was performed. Ether (Et$_2$O, 50 ml) was added and the mixture was sufficiently stirred and dissolved, and then SnBr$_4$ (tin (IV) tetrabromide, 50 mmol, 6.56 mL) was added. Tributylamine (NBu$_3$, 100 mmol, 23.8 ml) was added to the mixture in an ice bath, and after stirring for 10 minutes, the ice bath was removed and the mixture was continuously reacted at room temperature for 1 hour. After the reaction, Et$_2$O was drained to obtain a catalyst C-3: (EDBP)SnBr$_2$(Et$_2$O)/HNBu$_3$Br, and yield >99%.

Synthesis of Catalyst C-4

After Et$_2$O was added to the catalyst C-3 and dissolved, hexane was slowly added and the mixture was stirred (hexane/Et$_2$O=50 mL/10 mL) to precipitate a large quantity of a yellow solid to obtain a catalyst C-4: (EDBP)SnBr$_2$ (Et$_2$O), and yield: 88%.

$^1$H NMR (CDCl$_3$, ppm) of the catalyst C-4: δ 7.34, 7.18 (dd, 4H, Ph, J=2.4 Hz); 4.64 (q, 1H, CH, J=6.4 Hz); 3.74 (q, 4H, OCH$_2$CH$_3$, J=6.8 Hz); 1.67 (d, 3H, J=6.8 Hz); 1.41 (s, 18H, C(CH$_3$)$_3$); 1.33-1.27 (m, 24H, C(CH$_3$)$_3$+OCH$_2$CH$_3$).

Synthesis of Catalyst C-5

MMPEP (2,2'-methylenebis(4,6-di(1-methyl-1-phenyl-ethyl)-phenol), 20 mmol, 13.5 g, manufacture method as described in *Macromolecules* 2001, 34, 6196-6201) was placed in a 250 mL flask, nitrogen substitution was performed, ether (Et$_2$O, 50 mL) was added, and the mixture was sufficiently stirred and dissolved, and then SnBr$_4$ (tin (IV) tetrabromide, 50 mmol, 6.56 mL) was added. Tributylamine (NBu$_3$, 100 mmol, 23.8 mL) was added to the mixture in an ice bath, and after stirring for 10 minutes, the ice bath was removed and the mixture was continuously reacted at room temperature for 1 hour. After the reaction, Et$_2$O was drained to obtain a catalyst C-5: (MMPEP)SnBr$_2$(Et$_2$O)/HNBu$_3$Br, and yield >99%.

Synthesis of Catalyst C-6

After the catalyst C-5 was stirred using toluene until dissolved, the mixture was concentrated to saturation, and then placed in a −18° C. environment to recrystallize to precipitate a large quantity of orange-yellow solid to obtain a catalyst C-6: (MMPEP)SnBr$_2$(Et$_2$O), and yield: 62%.

$^1$H NMR (CDCl$_3$, ppm) of the catalyst C-6: $^1$H NMR (CDCl$_3$, ppm): δ 6.97-7.36 (m, 24H, Ph); 3.48 (d, 1H, CH$_2$, J=13.6 Hz); 3.07-3.01 (m, 5H, CH$_2$+OCH$_2$CH$_3$); 1.67, 1.63 (m, 12H, CH$_3$), 1.39-1.33 (m, 18H, CH$_3$+OCH$_2$CH$_3$).

Experimental Example 1

Epoxy compound BDGE (1,4-butanediol diglycidyl ether, 100 g) and the catalyst C-1 (0.457 g, 0.4×10$^{-2}$ M, 0.08 mol %) were placed in a reaction vessel, and after the catalyst was sufficiently dissolved, CO$_2$ (1 atm) was introduced and the temperature was increased to 100° C. The mixture was continuously stirred and reacted for 24 hours and the reaction conversion rate obtained by $^1$H NMR spectral analysis was 99%. The detailed parameters and results are shown in Table 1 below.

Experimental Examples 2 to 6

The cyclic carbonate compound was synthesized according to the method of experimental example 1, but the catalysts used were respectively catalyst C-2 (experimental example 2), catalyst C-3 (experimental example 3), catalyst C-4 (experimental example 4), catalyst C-5 (experimental example 5), and catalyst C-6 (experimental example 6). The detailed parameters and the conversion rate of $^1$H NMR spectral analysis are shown in Table 1 below.

Experimental Example 7

A cyclic carbonate compound was synthesized according to the method of experimental example 4, but the concentration of the catalyst C-4 used was 0.8×10$^{-2}$ M (0.631 g, 0.16 mol %). The detailed parameters and the conversion rate of $^1$H NMR spectral analysis are shown in Table 1 below.

Experimental Examples 8 to 10

A cyclic carbonate compound was synthesized according to the method of experimental example 4, but the concentration of the catalyst C-4 used was 1.6×10$^{-2}$ M (1.263 g, 0.32 mol %). Moreover, the reaction temperature and time were respectively 100° C. and 8 hours (experimental example 8), 120° C. and 5 hours (experimental example 9), and 140° C. and 3 hours (experimental example 10). The detailed parameters and the conversion rate of $^1$H NMR spectral analysis are shown in Table 1 below.

Experimental Examples 11 to 13

Cyclic carbonate compounds were synthesized according to the method of experimental example 8, but the epoxy compounds used were changed to PPGDG (poly(propylene glycol)diglycidyl ether, 100 g) (experimental example 11), RDCE (resorcinol diglycidyl ether, 100 g) (experimental example 12), and DGEBA (diglycidyl ether of bisphenol-A, 100 g) (experimental example 13). Moreover, the reaction temperature and time were respectively 100° C. and 8 hours (experimental example 11), 100° C. and 24 hours (experimental example 12), and 100° C. and 24 hours (experimental example 13). The detailed parameters and the conversion rate of $^1$H NMR spectral analysis are shown in Table 1 below.

Experimental Examples 14 to 15

Cyclic carbonate compounds were synthesized according to the method of experimental example 8, but a co-catalyst TBAB (tetrabutylammonium bromide, 0.516 g, 1.6×10$^{-2}$ M, 0.32 mol %, Sigma-Aldrich) was further added, and the reaction temperature and time were respectively 100° C. and 5 hours (experimental example 14) and 140° C. and 2 hours (experimental example 15). The detailed parameters and the conversion rate of $^1$H NMR spectral analysis are shown in Table 1 below.

Comparative Example 1

Epoxy compound BDGE (100 g) and the catalyst SnBr$_4$ (0.175 g, 1.6×10$^{-2}$ M, 0.32 mol %, Sigma-Aldrich) were placed in a reaction vessel, and after the catalyst was sufficiently dissolved, $CO_2$ (1 atm) was introduced and the temperature was increased to 100° C. The mixture was continuously stirred and reacted for 24 hours and the reaction conversion rate obtained by $^1$H NMR spectral analysis is provided in Table 1 below.

Comparative Example 2

A cyclic carbonate compound was synthesized according to the method of comparative example 1, and another catalyst TBAB (0.516 g, 1.6×10$^{-2}$ M, 0.32 mol %) was further added. The detailed parameters and the conversion rate of $^1$H NMR spectral analysis are shown in Table 1 below.

Comparative Example 3

A cyclic carbonate compound was synthesized according to the method of comparative example 2 without the catalyst $SnBr_4$. The detailed parameters and the conversion rate of $^1$H NMR spectral analysis are shown in Table 1 below.

TABLE 1

| | Catalyst (M, ×10$^{-2}$) | Co-catalyst (M, ×10$^{-2}$) | Epoxy compound | Reaction temperature (° C.) | Reaction time (h) | Conversion rate (%) |
|---|---|---|---|---|---|---|
| Experimental example 1 | C-1 (0.4) | | BDGE | 100 | 24 | 99 |
| Experimental example 2 | C-2 (0.4) | | BDGE | 100 | 24 | 77 |
| Experimental example 3 | C-3 (0.4) | | BDGE | 100 | 24 | 99 |
| Experimental example 4 | C-4 (0.4) | | BDGE | 100 | 24 | 81 |
| Experimental example 5 | C-5 (0.4) | | BDGE | 100 | 24 | 99 |
| Experimental example 6 | C-6 (0.4) | | BDGE | 100 | 24 | 83 |
| Experimental example 7 | C-4 (0.8) | | BDGE | 100 | 24 | 96 |
| Experimental example 8 | C-4 (1.6) | | BDGE | 100 | 8 | 98 |
| Experimental example 9 | C-4 (1.6) | | BDGE | 120 | 5 | 97 |
| Experimental example 10 | C-4 (1.6) | | BDGE | 140 | 3 | 97 |
| Experimental example 11 | C-4 (1.6) | | PPGDG | 100 | 8 | 99 |
| Experimental example 12 | C-4 (1.6) | | RDCE | 100 | 24 | 94 |
| Experimental example 13 | C-4 (1.6) | | DGEBA | 100 | 24 | 77 |
| Experimental example 14 | C-4 (1.6) | TBAB (1.6) | BDGE | 100 | 5 | 98 |
| Experimental example 15 | C-4 (1.6) | TBAB (1.6) | BDGE | 140 | 2 | 94 |
| Comparative example 1 | SnBr$_4$ (1.6) | | BDGE | 100 | 24 | 27 |
| Comparative example 2 | SnBr$_4$ (1.6) | TBAB (1.6) | BDGE | 100 | 24 | 63 |
| Comparative example 3 | | TBAB (1.6) | BDGE | 100 | 24 | 54 |

It can be known from Table 1 that, the catalyst of the disclosure can have better conversion rate for cyclic carbonate without strict reaction conditions.

Moreover, the turnover frequencies (TOF) of experimental example 8, comparative example 1, and comparative example 3 using different catalysts at the same concentration were compared, and the results are shown in Table 2 below.

In particular, TOF=[(moles of epoxy functional group/moles of catalyst)×reaction conversion rate]/reaction time).

TABLE 2

| | Catalyst (M, ×10$^{-2}$) | Reaction temperature (° C.) | Reaction time (h) | Conversion rate (%) | TOF (h$^{-1}$) |
|---|---|---|---|---|---|
| Experimental example 8 | C-4 (1.6) | 100 | 8 | 98 | 76 |
| Comparative example 1 | SnBr$_4$ (1.6) | 100 | 24 | 27 | 7 |
| Comparative example 3 | TBAB (1.6) | 100 | 24 | 54 | 14 |

It can be known from Table 2 that, the TOF of the catalyst of the disclosure is at least 5 times higher than that of the current commercial catalyst.

Based on the above, in the disclosure, a penta-coordinated catalyst is developed to increase cycloaddition reaction activity of greenhouse gas carbon dioxide, reduce reaction activation energy, and increase production efficiency of cyclic carbonate.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A catalyst, comprising a metal complex represented by formula (I):

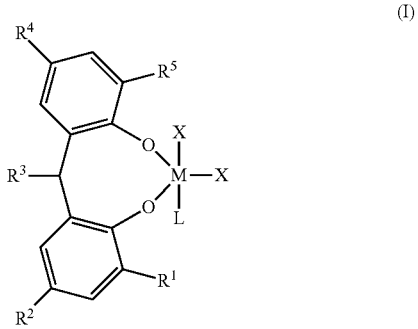

wherein $R^1$, $R^2$, $R^4$, and $R^5$ are independently a C1-C25 alkyl group, a C1-C25 alkoxy group, a C3-C8 cycloalkyl group, a C6-C25 aryl group, a C6-C25 aryloxy group, a C7-C25 aralkyl group, a C7-C25 aralkoxy group, or halogen; $R^3$ is hydrogen, a C1-C25 alkyl group, a C3-C8 cycloalkyl group, a C6-C25 aryl group, a C6-C25 aryloxy group, a C7-C25 aralkyl group, or a C7-C25 aralkoxy group; M is Sn or Ti; X is Cl, Br, I, or OAc; and L represents ether or furan.

2. The catalyst of claim 1, further comprising a quaternary ammonium salt represented by formula (II):

wherein $R^6$, $R^7$, and $R^8$ are independently a C1-C25 alkyl group or a C6-C25 aryl group; and X is Cl, Br, I, or OAc.

3. The catalyst of claim 2, wherein a molar ratio of the quaternary ammonium salt to the metal complex is between 0.01 and 5.

4. The catalyst of claim 1, wherein M in formula (I) is tin, and X is Cl or Br.

5. The catalyst of claim 1, wherein $R^1$, $R^2$, $R^4$, and $R^5$ in formula (I) are independently a C1-C4 alkyl group, a C1-C4 alkoxy group, a C5-C6 cycloalkyl group, a C6-C10 aryl group, a C6-C7 aryloxy group, or a C7-C9 aralkyl group; $R^3$ is hydrogen, a C1-C4 alkyl group, a C5-C6 cycloalkyl, a C6-C10 aryl group, a C6-C7 aryloxy group, or a C7-C9 aralkyl group.

6. A synthesis method of cyclic carbonate, comprising:
reacting an epoxy compound with a carbon dioxide to form a cyclic carbonate compound in the presence of the catalyst of claim 1.

7. The synthesis method of cyclic carbonate of claim 6, wherein the epoxy compound is represented by formula (III):

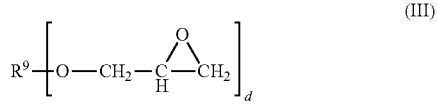

wherein d is an integer of 1 to 6; and $R^9$ is a functional group that can be substituted of an aliphatic compound, an alicyclic compound, an aromatic compound, an alkyl-substituted aromatic compound, polyether oligomer or polyester oligomer, or a combination thereof.

8. The synthesis method of cyclic carbonate of claim 6, wherein a concentration of the catalyst is between $1\times10^{-6}$ mol % and 1 mol %.

9. The synthesis method of cyclic carbonate of claim 6, wherein a pressure of the carbon dioxide is between 0.1 atm and 100 atm.

10. The synthesis method of cyclic carbonate of claim 6, wherein a reaction temperature for forming the cyclic carbonate compound is between 50° C. and 200° C.

11. The synthesis method of cyclic carbonate of claim 6, wherein a reaction time for forming the cyclic carbonate compound is between 2 hours and 30 hours.

12. The synthesis method of cyclic carbonate of claim 6, wherein the epoxy compound is poly(propylene glycol) diglycidyl ether (PPGDG), resorcinol diglycidyl ether (RDCE), diglycidyl ether of bisphenol-A (DGEBA), or 1,4-butanediol diglycidyl ether (BDGE).

* * * * *